US005436144A

United States Patent [19]

Stewart et al.

[11] Patent Number: 5,436,144

[45] Date of Patent: Jul. 25, 1995

[54] PROCESS FOR PERFORMING PCR IN MAMMALIAN CELLS

[75] Inventors: Carleton Stewart, Orchard Park; Earl A. Timm, Jr., Angola, both of N.Y.

[73] Assignee: Health Research, Inc., Buffalo, N.Y.

[21] Appl. No.: 208,795

[22] Filed: Mar. 9, 1994

Related U.S. Application Data

[63] Continuation of Ser. No. 682,446, Apr. 8, 1991.

[51] Int. Cl.$^6$ .......................... C12Q 1/68; C12P 14/34

[52] U.S. Cl. .......................................... 435/91.2; 435/6

[58] Field of Search .................................. 435/6, 91.2

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,889,818 | 12/1989 | Gelfand et al. | 435/194 |

OTHER PUBLICATIONS

Timm, E. A. et al. Genotyping cells by flow cytometry using PCR techniques, Abstracts for the XIV International Meeting of the Society for Analytical Cytology, Mar. 18–23, 1990, Cytometry (Suppl. 4) p. 79.

Ramphal, R. et al. *Pseudomonas aeruginosa* Recognizes Carbohydrate Chains Containing Type 1 . . . Infect. Immūn. (Feb. 1991) 59:700–704.

Harlow, E. et al. Antibodies: A Laboratory Manual (1988) p. 179.

Spann, W. et al.,–In Situ Amplification of Single Copy Gene Segments in Individual Cells by the Polymerase Chain Reaction, Infection 19, No. 4, 46–48 (1991).

Lo, Y–M. D. et al., Rapid Production of Vector–Free Biotinylated Probes Using the Polymerase Chain Reaction, Nucleic Acids Research 16:8719, (1988).

Feorino, P. M. et al., Lymphadenopathy Associated Virus Infection of a Blood Donor–Recipient Pair with Acquired Immunodeficiency Syndrome, Science 225:69–72 (1984).

Coombs, R. W. et al., Plasmia Viremia in Human Immunodeficiency, NEJM 321:1626–1631 (1989).

Saiki, R. K. et al., Primer Directed Enzymatic Amplification of DNA with a Thermostable DNA Polymerase, Science 239:487 (1988).

Schriever, F. et al., Isolated Human Follicular Dendritic Cells Display a Unique Antigenic Phenotype, J. Exp. Med. 169:2043–2058 (1989).

Frye, R. A. et al., Detection of Amplified Oncogenes by Differential PCR, Oncogene 4:1153–1157 (1989).

Saiki, R. K. et al., Analysis of Enzymatically Amplified B–globin and HLA–DOαDNA with Allele–Specific Oligonucleotide Probes, Nature 324:163–165 (1986).

Almoguera, C. et al., Most Human Carcinomas of the Exocrine Pancreas Contain Mutant c–K–ras Genes, Cell:549–554 (1988).

Bauman, J. G. J. et al., Flow Cytometry of Fluorescent In Situ Hybridization to Detect Specific RNA and DNA Sequences, Acta Histochemica Suppl. 37:65–69 (1989).

Singer, R. H. et al., Optimization of In Situ Hybridization Using Isotopic and Non–Isotopic Detection Methods, Biotechniques 4:230 (1986).

Terott, L. H. et al., In Situ Transcription: Specific Synthesis of Complementary DNA in Fixed Tissue Sections, Science 240:1661–1664 (1988).

Kawasaki, E. S. et al., Diagnosis of Chronic Myeloid and Acute Lymphocytic Leukemias by Detection of Leukemia–Specific mRNA Sequences Amplified In Vitro., Proc. Nat'l. Acad. Sci. USA 85:5698–5702

(List continued on next page.)

*Primary Examiner*—Margaret Parr
*Assistant Examiner*—David Schreiber
*Attorney, Agent, or Firm*—Michael L. Dunn

[57] ABSTRACT

A process is provided for performing polymerase chain reactions inside of intact cells. Measurement of genetic parameters and observation of genetic properties while maintaining the integrity of the DNA or RNA in a cell is accomplished by passing a suspension of cells through a flow cytometer wherein the properties and parameters can be measured on a cell by cell basis.

2 Claims, 9 Drawing Sheets

FIG 8

OTHER PUBLICATIONS (1988).
Singer, R. H. et al., Actin Gene Expression Visualized in Chicken Muscle Tissue Culture by Using In Situ Hybridization with a Biotinylated Nucleotide Analog, Proc. Nat'l. Acad. Sci. USA 79:7331–7335 (1982).
Mullis, K. B. et al., Specific Synthesis of DNA In VItro Via a Polymerase–Catalyzed Chain Reaction, Methods in Enzymology 155:335–351 (1987).
Pinkel, D. et al., Cytogenetic Analysis Using Quantitative High Sensitivity, Fluorescence Hybridization, Proc. Nat'l. Acad. Sci. USA 83:2934–2938 (1986).
Bakkus, M. et al., Detection of Oncogene Expression by Fluorescent In Situ Hybridization in Combination with Immunofluorescent Staining of Cell Surface Markers, Oncogene 4:1255–1262 (1989).
Haase, A. T., et al., Amplification and Detection of Lentiviral DNA Inside Cells, Proc. Nat'l. Acad. Sci. USA, 87:4971–4975 (1990).
Willman, C. L., et al., Differential Expression and Regulation of the c–src and c–for Protooncogenes in Myelomonocytic Cells, Proc. Nat'l. Acad. Sci. USA 84:4480–4484 (1987).

DNA sense        5'-C A A G T A T G C A T G-3'
DNA antisense    3'-A C C G A T A C G T A C-5'?

DNA sense        C A A G T A T G C A T G
DNA antisense    A C C G A T A C G T A C DNA sense        C A A G T A T G C A T G
RNA antisense    G U U G A U A G C U A C

PROCESS FOR PERFORMING PCR IN MAMMALIAN CELLS

The invention disclosed herein was made in the course of work done under the support of Grant No. AI 19490, awarded by the National Institute of Health.

This is a File Wrapper Continuation of application Ser. No. 07/682,446, filed Apr. 8, 1991.

BACKGROUND OF THE INVENTION

In the last decade, molecular biology has made a major impact in the understanding of normal cell function and alterations that take place in disease. The current technologies require the extraction of DNA or RNA from cells prior to analysis. In heterogeneous populations of cells, the actual cells that express a particular gene or have a particular gene amplified or mutated or translocated cannot be identified. In situ hybridization of genetic probes to intact cells or chromosomes fixed to microscope slides has been successfully performed to measure genetic parameters on an individual cell or chromosome basis. This is disclosed by Singer et al. in *Biotechniques* 4:230, 1986; Singer et al. in *Proc. National Acad. Sci.* 79:7331–7335, (1982); and Bakkus et al. in *Oncogene* 4:1255–1262, (1989).

The polymerase chain reaction (PCR) is extensively used to amplify genomic DNA extracted from cells to provide genetic material for further study. This has been disclosed by Saiki et al. in *Science* 239:487 (1988); by Frye in *Oncogene* 4: 1153–1157 (1989); by Saiki et al. in *Nature,* 324, 163–165 (1986); by Almoguera et al. in *Cell* 549-554 (1988); and Mullis et al. in *Methods in Enzymology* 155: 335–351 (1987). The PCR is also disclosed in U.S. Pat. Nos. 4,683,195 and 4,683,202, the disclosures of which are incorporated herein by reference. More recently RNA has been studied by first using reverse transcriptase to convert RNA into DNA and then to amplify the DNA using the PCR as disclosed by Schriever et al. in *J. Exp. Med.* 169:2043–2058 (1989) and Kawasaki et al. in *Proc. Nat'l. Acad. Sci USA* 85:5698–5702 (1988). These procedures utilize RNA or DNA that is first extracted from intact cells. Further manipulation takes place in a cell free environment wherein all reaction substances are in solution. This technology has also been applied to the amplification of viral RNA using a reverse transcriptase to make a cDNA as disclosed by Feorino et al. in *Science* 225:69–72 (1984) and Coombs et al. at *NEJM* 321:1626–1631 (1989). Tecott, et al. disclose in *Science* 240:1661–1664 (1988) that they have carried out the reverse transcriptase step in paraformaldehyde fixed intact cells using a radioactive nucleotide for detection. Frye, et al. in *Oncogene* 4:1153–1157 (1989) insinuated that they performed PCR on intact cells but they provided no methodology or data for performing this task. Since their evidence for a reaction product was standard gel electrophoresis, it can be concluded they did not actually perform the PCR in the cells themselves. Bauman, et al. in *Acta Histochemica Suppl.* 37:65–69 (1989) suggested that Flow Cytometry would provide several advantages for measuring specific RNA and DNA sequences, and provide examples using in situ hybridization but they did not use the polymerase chain reaction. Finally, Haase et al. in *Proc. Nat'l. Acad. Sci. USA,* Vol. 87, pp 4971–4975, in Jul. 1990, disclosed conducting the PCR inside certain cells, but did not suggest measuring the cells with flow cytometry. The forgoing references are incorporated herein by reference as background information.

SUMMARY OF THE INVENTION

A purpose of this invention is that the entire polymerase chain reaction takes place inside the intact cell that is in suspension.

For the first time, the polymerase chain reaction (PCR) has been performed inside intact cells to amplify specific genetic material and the resulting cells were measured using flow cytometry. This method avoids first isolating the substrate by destroying the cell. This art is not an obvious extension of the PCR in solution because the cells must be fixed in such a way that they remain intact after many heating and cooling cycles. The cells must not be lost by adhesion or lysis during the process and, the reaction product must remain associated with the cell (and not leak out).

A method has been developed to perform this task in a cell suspension so that genetic material can be rapidly measured on a cell by cell basis using a flow cytometer as disclosed by Pinkel et al. in *Proc. Nat'l. Acad. Sci. USA* 83:2934–2938 (1986). For the measurement of gene expression, reverse transcriptase is used to produce c-DNA that is then amplified using the polymerase chain reaction (PCR). Genomic DNA is amplified directly using the polymerase chain reaction. The establishment of this methodology provides a means of molecular phenotyping on a cell by cell basis. Applications for this invention include the rapid measurement of inappropriate gene expression in neoplasia, quantitative measurement of gene expression, the measurement of gene rearrangement, and the measurement of viral infection on a cell by cell basis to name a few.

This invention primarily involves performing a polymerase chain reaction inside intact cells, that is, without removing DNA or RNA from the cell.

This invention involves a process for identifying intact cells that have been labeled in suspension with fluorescent genetic probes which comprise subjecting said cells to flow cytometry.

The invention further involves rapidly measuring genetic material on a cell by cell basis using flow cytometry.

DETAILED EMBODIMENT OF THE INVENTION

The Polymerase Chain Reaction (PCR):

The first step in the known PCR process is to determine the sequence of the RNA or DNA desired for amplification. There are several ways to perform this task. One common method is to obtain the sequence from a genomic data base such as GenBank (Genbank Submissions, Group T-10, Mail Stop K710, Los Alamos National Laboratories, Los Alamos, N. Mex. 87545). This is easiest when previously sequenced DNA data are available. A 100-500 base sequence can be selected for amplification, preferably a 200 to 300 base sequence.

Figure 1:
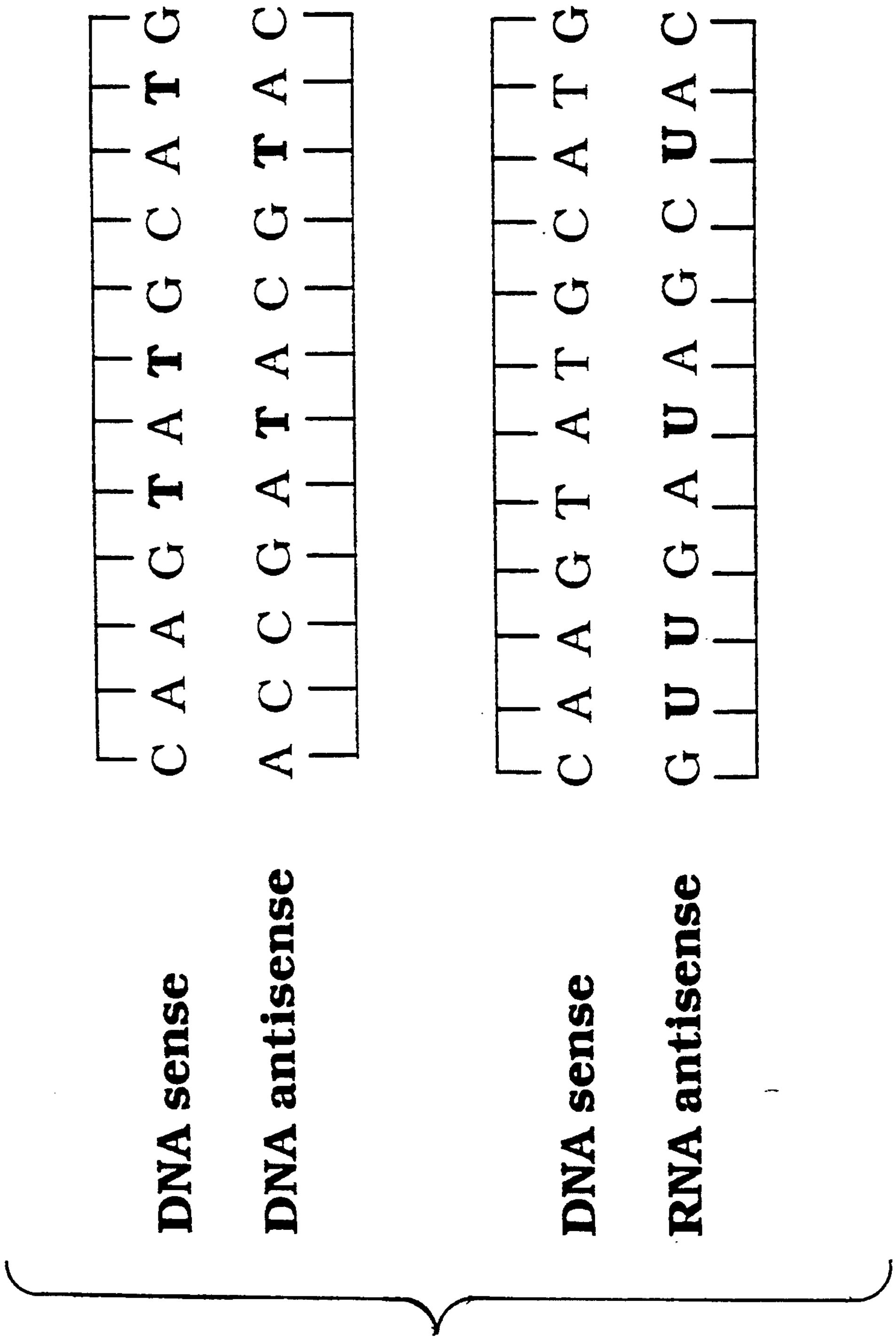
FIG. 1 depicts partial base pairing in DNA and RNA.

There are two strands of DNA that are bound together, a sense strand and an antisense strand. In RNA, there is only one strand and it is complementary (or opposite) in its base sequence to the sense strand of the DNA. In this regard, it is an antisense code. In DNA, four nucleotide bases are assembled in a unique order that makes up the sequence. The nucleoside bases are adenosine, thymidine, guanosine and cytidine. In RNA, uridine is substituted for thymidine. Each base is paired in a unique way between the sense and antisense strand and, as shown in FIG. 1, thymidine triphosphate, for DNA, or a uridine triphosphate, in RNA, is paired with an adenosine triphosphate and a cytidine triphosphate is paired with a guanosine triphosphate.

Figure 2:
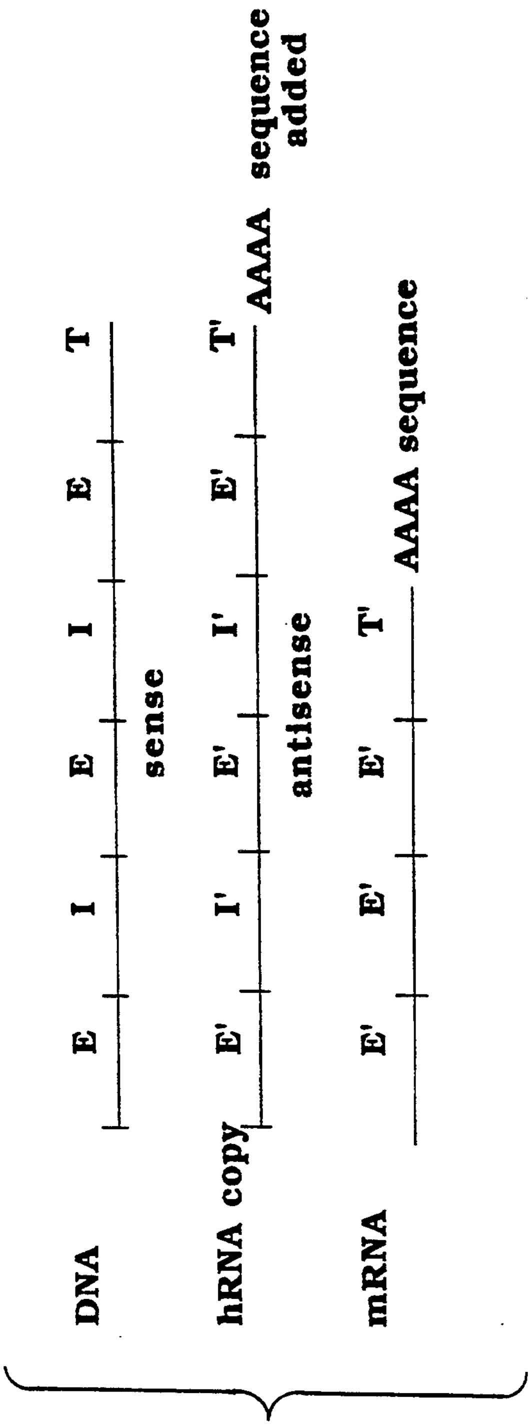
FIG. 2 shows transcription of a genetic sequence.

The process by which an RNA strand is produced from DNA within the cell is called transcription. In this process, the genetic sequence being copied contains exons (E) that are the coding regions for the product that are produced by the cell. These regions are separated by introns (I) that act as spacers. A schematic representation of such a genetic sequence is shown in FIG. 2. When the genetic sequence known as the "sense" strand is transcribed, an RNA copy is produced and the complimentary "antisense" strand contains both the exons and introns. This RNA is called heterogeneous RNA (hRNA) and it is found in the nucleus of the cell. At the end of a gene sequence, terminal sequences (T) and polyadenylated sequences (A) are found and are added at the 3′ end the hRNA. Heterogeneous RNA (hRNA) is the sequence of ribonucleic acids directly transcribed from the genomic DNA. This consists of the promoter sequences, the exons which are the actual coding region, the introns which are the non-coding spacer regions and the 3′ trailing sequences. The introns are removed by a process called post transcriptional modification producing messenger RNA (mRNA).

Figure 3:
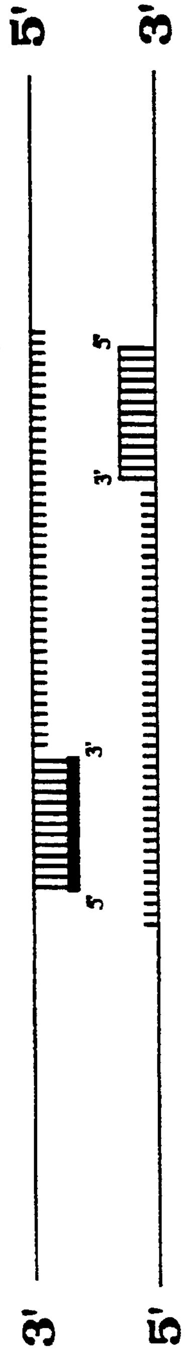
FIG. 3 shows primer attachment to DNA or RNA.

The second step in the known PCR process is to prepare two oligomers of 20–30 bases long (called primers) whose sequences are identical to the antisense end and the sense end respectively of the base sequence that is to be amplified. It is between these primers that the amplification occurs. A schematic representation of these primers attached to DNA prior to amplification is shown in FIG. 3.

Figure 4:
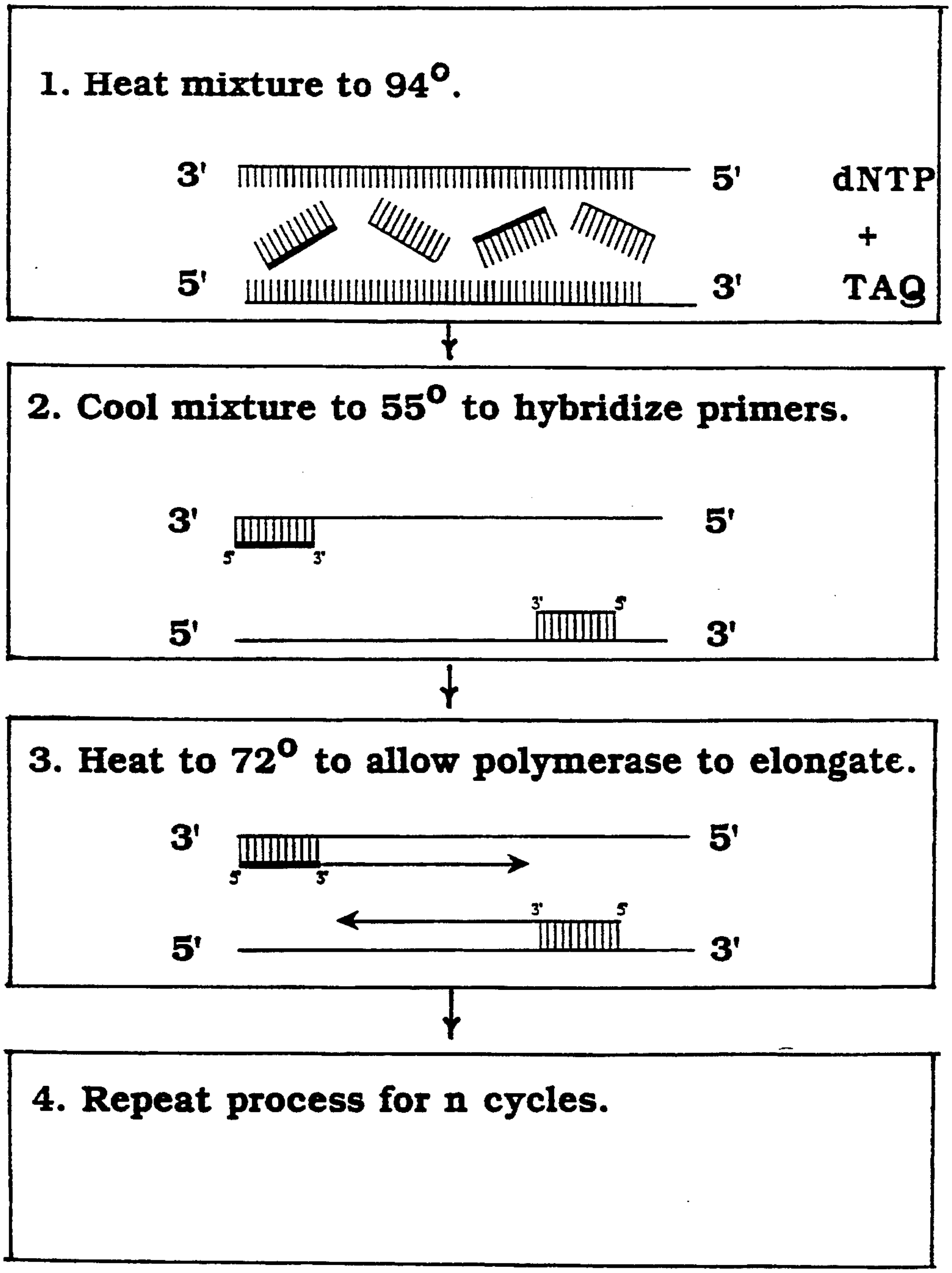
FIG. 4 shows how primers bind to their homologous DNA sequences, and undergo the polymerase chain reaction.

The third step in the known PCR process is to mix the DNA extracted from the cell with the two primers, a heat stable DNA polymerase (TAQ) (Perkin-Elmer Cetus, Norwalk, Conn.) and the 4 nucleotide triphosphates (dNTP). TAQ1 is Thermus aquaticus 1 DNA Polymerase which is a thermo-stable DNA polymerase developed by Perkin-Elmer Cetus Corporation, 761 Main Ave., Norwalk Conn. 06859. It is used extensively in polymerase chain reaction experiments because of the high heat stability of the enzyme. This type of polymerase is described in U.S. Pat. No. 4,889,818, the disclosure of which is incorporated by reference. The mixture is heated to allow the DNA to unwind (called melting). As shown in FIG. 4, upon cooling, the primers bind to their homologous sequences (called hybridization). In the presence of DNA polymerase, two new strands are produced as elongation of the DNA proceeds in a 5′ to 3′ direction from the 3′ end of the primer. The mixture is reheated, new primers attach to the newly synthesized strands and the process is repeated. After each cycle, the total number of strands is doubled i.e., the copies are geometrically amplified. A product is formed that is of a size which includes both the sense and antisense primers and all nucleotides between the two. For example, if two 30 base primers are used and the number of sequences between is 140, a 200 base pair (double stranded) product is produced by the PCR reaction.

Microscopy:

Visual analysis of the samples can be done using a fluorescence microscope such as a Nikon Optiphot (Nikon Inc. Instruments Group, Garden City, N.Y. 11530) . Light from an ultraviolet (UV) lamp is passed through a filter that allows only the desired wavelength of light to pass. This wavelength of light is used to excite the fluorescent dye in the sample and this dye then emits another specific wavelength of light that can be detected visually. An example of a fluorescent dye is fluorescein which absorbs visible light at a wavelength of 488 nanometers (nm) and then emits light at a wavelength of 520 nm. The 520 nm light is seen as a green fluorescence in the sample. The observer can visually detect changes in the fluorescent intensity but this intensity cannot be easily quantitated by the observer. The use of a flow cytometer is used to accomplish that task.

Flow Cytometry:

A flow cytometer is an instrument that will measure fluorescence of individual cells as they pass in single file through a light source (usually a laser beam). Antibodies labeled with fluorescent dyes directed against cell antigens, fluorescent dyes that label specific substrates in the cell and fluorochromes that are sensitive to ions have all been used to label specific cell populations or molecules within cells for identification and evaluation of function. Flow cytometry can also be used to sort cells.

As cells, labeled with a fluorochrome attached in some way to the desired component, pass through the laser beam, the fluorochrome is excited. The emission is detected orthogonally (perpendicular) to the laser beam as the light passes through a focusing lens system and spectral filters to selectively detect the desired wavelength.

The light is then detected by a photomultiplier tube that integrates all the fluorescence that passes through the color bandpass filter. Nonspecific cellular fluorescence called autofluorescence appears yellow to the eye but there is a significant green component to it and this component is passed along with the green fluorescein fluorescence from fluorescein through the bandpass filter. Thus, the flow cytometer detects both the autofluorescence and the specific fluorescence from the component that is stained with fluorescein. If the fluorescence of the stained component is too low, it will not be resolved from the autofluorescence. A method to amplify the fluorescence of the desired component above the autofluorescence and other nonspecific fluorescence has been developed.

Factors that affect intact cell recovery are formamide and high standard saline citrate (SSC) concentration. Increasing the formamide concentration from zero percent will lower the temperature at which double stranded DNA melts (comes apart into two separate strands). Using higher concentrations of formamide allows the use of lower reaction temperatures during hybridization. Too much formamide in the buffer will cause the cells to aggregate irreversibly at temperatures warmer than 50 degrees centigrade. A high SSC concentration (>1x) in combination with a high formamide amount (40–50%) only serves to aggravate this problem. Some cell loss is the result of increased stickiness that causes them to adhere to the reaction tube or to aggregate. This cell loss can be reduced by transferring the cells to a 12–75 mm tube containing Tris HCl pH 8.3+500 μg/ml nuclease free bovine serum albumin buffer (TBB) prior to centrifugation.

Formamide could be eliminated if primers were hybridized to RNA for 1.5 hours at 65° at a stringency of 4X SSC. The actual temperature should be adjusted depending on the primer length and CG (deoxycytidine, deoxyguanosine) content. Time of incubation and temperature were not found to be critical factors resulting in cell loss unless cells were held for prolonged periods at high temperature. Thus, cells held at 95° for over 10 minutes begin to disintegrate. In contrast, thermocycling the cells between 50° and 95° over a 7 minute period did not produce cell loss or disintegration. The presence of protein, e.g., 500 μg/ml bovine serum albumin (nuclease free), in the washing solution reduced cell loss by adhesion and aggregation.

Another important consideration when doing PCR in situ is the concentration of the target DNA. When performing PCR in solution the geometric increase in product concentration with each cycle does not continue indefinitely. Usually above 30–35 cycles, the rate of increase in product concentration will decrease and asymptotically approaches zero. This is because there is hybridization between complementary products occurring more readily than between the primer and product. This reaction is highly dependent on concentration.

This feature of the PCR is disadvantageous for performing the reaction within a cell where the solution volume is several orders of magnitude less than customarily used. The starting template is already at a very high concentration per unit volume in the cell, and after 10–15 cycles no further amplification within the cell can be achieved using standard PCR technique.

To eliminate this problem, single chain elongation is employed. This is accomplished by using a single primer so that only one strand of DNA is produced. The result is a product with no complementary strand and therefore, there is no competition between primers and complementary strands during annealing. While geometric amplification does not occur and each cycle produces only one copy per template, the number of cycles is not as limiting as with standard PCR.

Utilizing this approach, however, undesired products can also be produced and expanded. So that these undesired products are not detected, a labeled probe to the desired product is used to read out the system. Several approaches for producing these probes are described hereinafter.

Examples

The system chosen to demonstrate that gene expression can be performed inside intact cells using the PCR, and that the reaction can be quantified using flow cytometry was to induce and measure the oncogene fos in macrophages stimulated by the growth factor CSF-1. Fos is a nuclear protein that is made very early in the cell cycle following stimulation of the cell by specific growth factors. One of these growth factors is CSF-1 or Colony Stimulating Factor also known as m-CSF (Macrophage-Colony Stimulating Factor). This system provides the proof of principle claimed in this invention. This system can measure changes in the levels of fos mRNA within the cell.

Bone marrow cells were obtained from $C_3H$ mouse femurs as previously described by Willman et al. in *Proc. Nat'l. Acad. Sci. USA* 84:4480–4484 (1987). $C_3H$ was the strain of mouse used for this study. The bone marrow cells were suspended at a concentration of $8\times10^4$ cells/ml in a MEM (alpha Minimum Essential Medium) supplemented with 20% fetal bovine serum and 20% L-929 cell conditioned medium (LCM). The L929 mouse fibroblast culture is a source of CSF-1. The conditioned medium is a rich source of the specific growth factor CSF1 for macrophages, as disclosed by Willman, C. L. et al. in *Proc. Nat'l. Acad. Sci. USA* 84: 4480–4484 (1987). The cells were plated (15ml) in 100 mm plastic petri dishes and incubated for 6 days at 37° in 7% $CO_2$ in air. At this time, a subconfluent monolayer of macrophages cover the dish. The cells are at a point where the ingrowth potential has not reached its maximum for the amount of nutrients provided. On day 6, the medium was changed (12.0 ml) to MEM supplemented with 20% fetal bovine serum to produce quiescent cells. Twenty four hours later, 3.0 ml of L-929 cell conditioned medium was added to half the dishes. Cells were removed from these dishes from 25 to 35 minutes later to produce a narrow time window with a median time of 30 minutes. This is the point at which there is a maximum expression of the fos mRNA in cells stimulated by CSF-1. Control cells that received no LCM were then harvested. Harvesting was performed by first aspirating the suspending medium. A jet stream from a 20 ml syringe with 25 gauge needle attached filled with PBS (phosphate buffered saline) was directed systematically across the entire plate to remove the cells. Cells were pooled into a 50 ml centrifuge tube and 45 ml of cell suspension was mixed with 5 ml of 10% ultrapure formaldehyde (Polysciences, Inc., Warrington, Pa. 18976–2590). The cells were incubated for 30 minutes at 20°–25° C. and then centrifuged at 1500 XG for 3 minutes. For northern blot analysis, cells were removed from the plates using guanidinium hydrochloride and processed as previously described by Willman et al.

Hybridization of Primers

The cell pellet was resuspended in 1XSSC (0.15 M NaCl+0.015M sodium citrate at pH 7.0) with 500 μg/ml BSA (bovine serum albumin, nuclease free, Gibco/BRL, 8400 Helgerman Court, Gaithersburg, Md. 20877) at $5\times10^6$ cells/ml. A volume of cell suspension containing $1\times10^6$ cells was transferred to a 1.7 ml microcentrifuge tube and then the tube was centrifuged. All supernatant material was removed from the cell pellet and the cells were resuspended in 50 μl hybridization buffer (4XSSC, 800 units/ml RNasin (an Rnase inhibitor sold by Promega Corporation 2800 Woods Hollow Rd. Madison, Wis. 53711-5399), and 0.001M sodium phosphate pH 7.0. For RNA, 1–10 pmol of the sense oligo primer was added. The sense primer is a sequence of DNA bases that are designed to anneal to a specific area of the mRNA at its 3' or downstream end. This is a template for the reverse transcriptase enzyme to make a complementary copy of the mRNA (messenger RNA). The sequence was prepared using a DNA synthesizer at the Roswell Park Cancer Institute. The sequence is: TTG CCC CTT CTG CCG ATG CTC TGC GCT CTG CC SEQ ID NO:2. This is a short sequence from the coding region (exon) of the fos oncogene. Samples were incubated for 1.5 hours at 65° C. to hybridize the primers to the RNA. 3 ml of 2X SSC containing 500 μg/ml BSA (nuclease free) were added. The material was centrifuged and the supernatant was decanted. The cells were resuspended in 0.4 ml 1XSSC with 500 μg/ml BSA 0.4 ml vanadyl ribonucleosides (20mM) was added to inhibit RNases. The product was stored at 4° for 18 hours.

Reverse Transcription for RNA:

The cells were centrifuged and resuspended in 3 ml of 50 mM Tris-HCl (Tris [hydroxymethyl] aminomethanane+hydrochloric acid to adjust pH) at pH 8.3 containing 500 μg/ml BSA (TBB). The cells were centrifuged and all the supernatant material was removed. The cells were resuspended in 50 μl of the reverse transcription solution (RTS) at 37°. This solution was TBB (Tris-HCl, BSA buffer) containing 1.5 mM MgCl, 40 mM KCl, 1.0 mM Dithiothreitol, 400 μM dATP (deoxyadenosine), 400 μM dCTP (deoxycytidine), 400 μM dGTP (deoxyguanosine), 400 μM TTP (deoxythimidine), 40 units RNasin, and 60 units Avian Myoblastosis (AMV) reverse transcriptase (Life Sciences, Inc. St. Petersburg, Fla.) The cells were incubated for 4 hours in a 96 well microtiter plate and transferred to a 12×75 mm tube. 3 ml of TBB was added, the cells were centrifuged and the supernatant material was removed. The pellets were resuspended in 3 ml TBB and stored at 4° until ready to proceed to the next step.

Polymerase Chain Reaction in Accord with the Invention.

The cells were centrifuged, the supernatant material was removed and the cells were resuspended in 0.5 ml TBB. The cells were transferred to 0.65 ml siliconized conical centrifuge tube. The cells were centrifuged to remove all supernatant material and the cell pellet was resuspended in 50 μl of TBB containing 1.5 mM MgCl, 40 mMKCl, 200 μM dATP, 200 μM dTTP, 200 μM cCTP, 200 μM dGTP, 40 pmol sense oligo primer, 40 pmol antisense oligo primer and 5 units TAQ I DNA polymerase. The antisense primer is a sequence of DNA bases analogous to the bases found in the 5' or upstream area of the mRNA. The sequence was TCC CCA CGG TGA CAG CCA TCT CCA CCA GCC C SEQ ID NO:2. It was incubated 20°–25° C. for 1 hour.

Overlay sample with 150 μl mineral oil and thermocycle:

| | | Temperature | Time |
|---|---|---|---|
| Step | Initialization | 94° C. | 1 min |
| Cycles | Step 1 | 94° C. | 1 min |
| | Step 2 | 55° C. | 2 min |
| | Step 3 | 72° C. | 2 min |
| Hold Sample | Soak | 4° C. | indefinite |

n step cycles (step 1 through step 3) were performed. Cells may be held in the soak cycle until time for further processing.

After the desired number of thermocycles, the cell suspension was removed from under mineral oil with a pipettor. Transfer cells to 12×75 mm tube and add 3.0 ml PAB (phosphate buffered saline containing 0.1% sodium azide and 0.5% bovine serum albumin). The cells were centrifuged, and the supernatant material was discarded. The cell pellet was resuspended in 3 ml PAB, and incubated 20°–25° for 30 minutes. The cells were centrifuged and the supernatant material was discarded. The cells were resuspended in PAB for storage.

Staining Reaction Product:

Fluorescein has been the fluorescent dye used in this process although other fluorescent dyes can be substituted to obtain the desired fluorescence excitation and emission spectrum. These other dyes can include phycoerythrin (PE) and a phycoerythrin-texas red (TR) conjugate, allophycocyanin or other dyes under development.

In one process, a biotinylated dNTP (where N is a variable that stands for one of the following bases: A=adenine, C-cytosine, G-guanine, T-thymine, U-uracil) was substituted for one of the dNTP's during the in situ PCR. This substitution can be made in both the reverse transcription reaction mixture as well as in the PCR reaction. Biotin-16- dUTP (Boehringer-Mannheim Biochemicals, P.O. Box 50414, Indianapolis, Ind. 46250) has provided the best reaction product. This is a molecule of the nucleotide deoxyuridine to which a molecule of biotin has been attached by a 16 atom linker arm. dUTP can be substituted for dTTP in a DNA sequence. A ratio of 65 percent dTTP to 35 percent Biotin-16-dUTP was used during the PCR. After obtaining the washed cell pellet, at the end of the reaction above, the cells were resuspended in 50 μl TBB containing 1 μg/ml of fluoresceinated avidin. Avidin, a protein found in eggs, has a high affinity for the molecule biotin. This provided the basis for biotin avidin labelings as in this case where the avidin has several molecules of fluorescein attached. The cells were incubated for 30 minutes at 4°, 3 ml PAB is added and the cells recentrifuged. The pellet was resuspended in 3 ml PAB, incubated 1 hour at 4° C., centrifuged and the pellet was resuspended in 0.3–0.5 ml PAB for analysis by flow cytometry.

In a second process, a biotinylated DNA probe prepared separately using a PCR in solution was hybridized directly to the PCR reaction product. The biotinylated probe was detected using an avidin containing a fluorescent dye such as fluorescein. The biotinylated probe was synthesized in solution using the same oligonucleotides as primers during the PCR. The template was provided by Genomic DNA. The probes in this case would have been labeled using the polymerase chain reaction to incorporate Biotin-16-dUTP into the product. A ratio of 65 percent dTTP to 35 percent Biotin-16-dUTP was used during the PCR. Probes obtained from plasmids that have been nick translated or probes produced by other methods (16) can also be used.

In a third process, oligo nucleotide probes were synthesized that have one of the nucleotides with a linker molecule that can be used for the direct attachment of fluorescent dyes such as fluorescein. The amount of signal depended upon the amount of "linked" nucleotides incorporated into the oligonucleotide.

In a fourth process, probes were also produced by the PCR using deoxyuridine triphosphate (dUTP) linked with the plant steriod digoxigenin (Dig). The Dig-11-dUTP was developed for Boehringer-Mannheim Biochemicals (address above) and they have produced a monoclonal antibody labeled with fluorescein that is specific for the dig steriod. This plant steriod did not seem to have an animal equivalent. Therefore the background noise caused by nonspecific labeling of the antibody was lower. Consequently, the signal from the product was more distinct in this case.

Results of the Process:

Two kinds of fluorescence can be distinguished microscopically. For microscopy, the cells were attached to microscope slides using a Cytospin™ Centrifuge (Shandon Inc. Pittsburgh, Pa. 15275). A small sample of the cell suspension was placed in the Cytospin and the sample was then centrifuged at 1000 rpm for 10 minutes. The slide was dried briefly and then the spot of cells on the slide was covered with 10 ul of a 50:50 mix of phosphate buffered saline (PBS) and glycerol. Finally, a slip cover was placed over the cells and the slide was viewed using the fluorescence microscope. The fluorescence associated with specific fluoresceinated probes had a green color while that associated with autofluorescence had a more yellow color. The color seen in the microscope (green or yellow) depended on the dominant form of fluorescence expressed in a cell. Using a flow cytometer, all the fluorescence passing through selected bandpass filters was integrated and spacial localization of specific fluorescence was lost. Nonspecific cellular autofluorescence that appears yellow to the eye, may have a significant green component to it and, this component was passed along with the green fluorescence from fluorescein through the band pass filter. Thus, the flow cytometer detected both the green component of the autofluorescence and the specific green fluorescence from the component that was stained with fluorescein. Furthermore, fluorescein avidin or fluorescein antibody can non-specifically bind the undesired components within the cell. The fluorescence of the stained component may be intense in a small area but may not be a large fraction of the total cellular autofluorescence and non-specific stained components that are more diffuse. A method to amplify the specific fluorescence of the desired component above the autofluorescence and other nonspecific fluorescence has been developed using the PCR.

Figure 5:
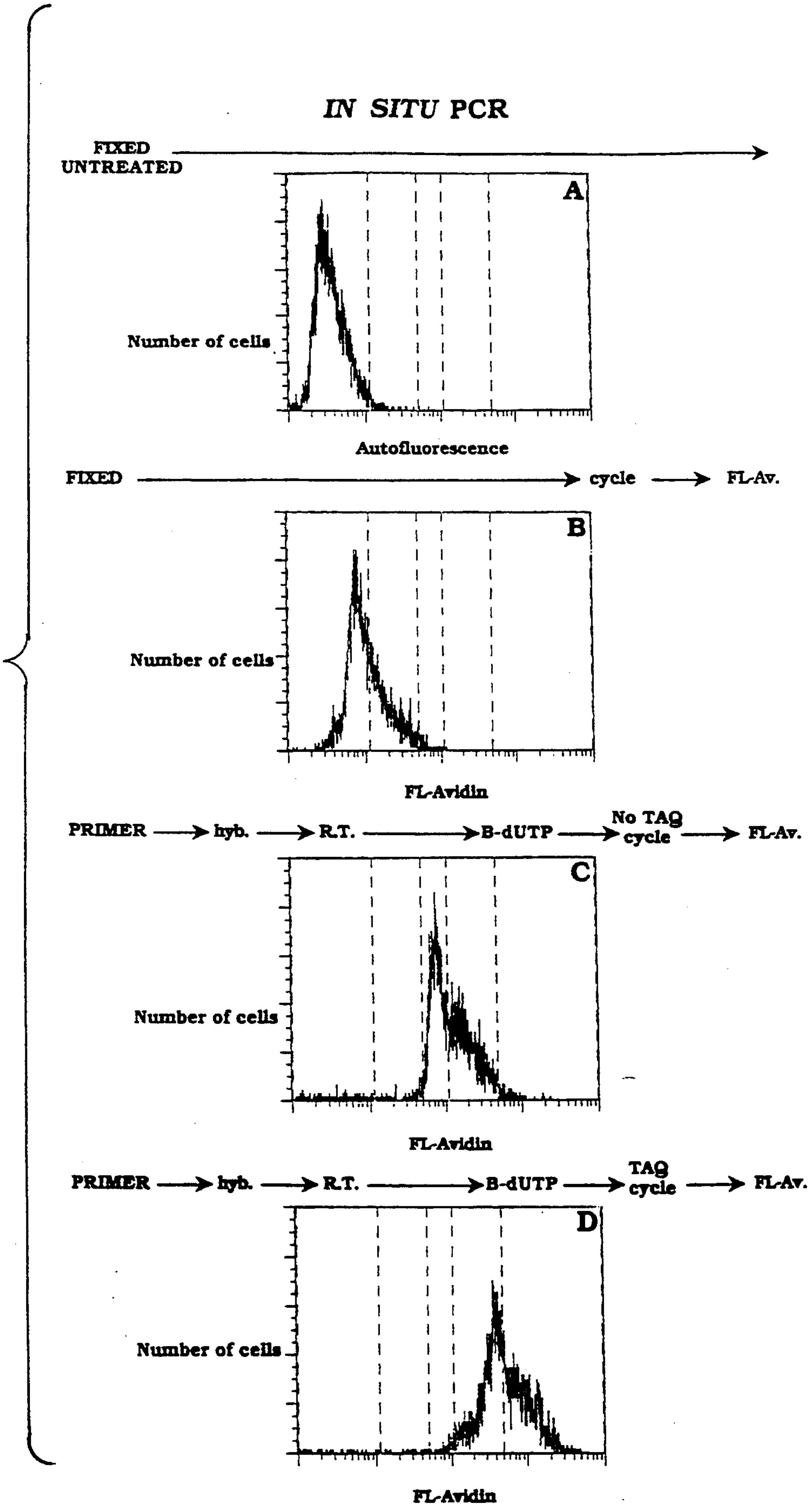
FIG. 5 shows the results of in situ PCR's and the various controls.

FIG. 5 shows the results of the first process in which the biotin-16-dUTP was incorporated into the product during the in situ PCR.

As shown in FIG. 5A, fixed cells exhibited the lowest amount of autofluorescence. Taking this as the baseline, the effect of the various procedures on cellular fluorescence was compared. In B, these cells were cycled 15 times and then stained with fluoresceinated avidin-DCS, (FL-Avidin, Vector Laboratories, Inc., 30 Ingold Rd., Burlingame, Calif. 94010). This is a molecule of avidin-DCS to which a fluorescein molecule has been attached. The CS stands for cell sorter grade. Cellular fluorescence increased by a factor of 3.1. In C, the primers were hybridized and then underwent reverse transcription in the absence of B-dUTP. After washing cells, B-dUTP, dTTP (30:70 mix), the other dNTP's and the primers were added to the cells and cycled 15 times. Cells were washed and stained with FL-Avidin DCS. This produced a 36 fold increase in cellular fluorescence even though there is no amplification reaction of any kind in the presence of B-dUTP because TAQ was not added. In D, the same procedure described for C was performed in the presence of TAQ. There is a 157 fold increase in cellular fluorescence. When cells used in FIG. 5D were viewed under a microscope, there was a specific green fluorescence of high intensity in the cytoplasm and in the nucleoli found in the nucleus.

Figure 6:
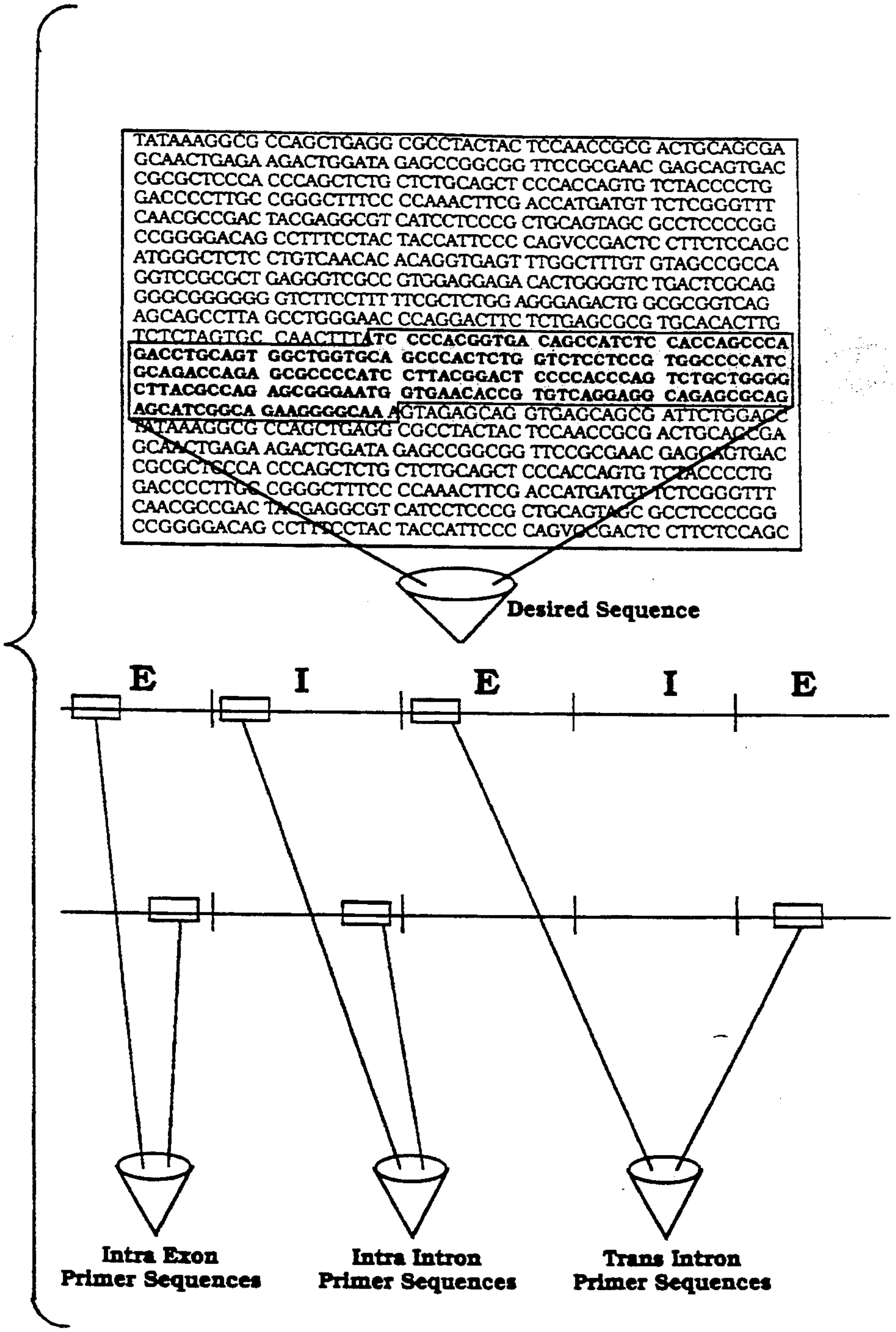
FIG. 6 shows a gene sequence and the location of possible primer sites for PCR.

In order to eliminate the high background, fluoresceinated probes have been designed, ranging from a 30 to 200 Mer. Mer refers to the length of a single stranded DNA or RNA molecule in number of nucleotides. The in situ PCR can then be performed in the absence of biotinylated nucleotides. After the PCR, the probe is hybridized to the cells. While any of the above described probes can be used, the best results can be obtained with the Dig-11-dUTP labeled probes. When preparing probes, detection of specific product can also be improved by using multiple labeled probes directed to the entire length of the desired sequence. For example, if the 2.2 kb message of the oncogene fos is to be detected, ten sequential labeled probes of 200 mer along the entire message can be synthesized by the PCR Strategies for Selective Amplification:

In order to specifically amplify the desired genetic material, the strategy employed in FIGS. 6 and 7 can be applied. The gene sequence is first obtained for the desired mRNA or DNA target and the appropriate primers were made.

As shown in FIG. 6, primers are made that are entirely contained within a single exon shown as "intra exon primer sequences." These primers result in the amplification of genomic DNA, heterogeneous RNA and messenger RNA since all three types contain the exon. Trans intron primers produce the same species of products but the mRNA product is smaller because the intron is missing.

As shown in FIG. 6, primers made to intra intron sequences to amplify DNA or hRNA are used in the PCR. Intra intron sequences are primer sequences located exclusively within the intron (non-coding region) of the DNA. For heterogeneous RNA, a cDNA must first be prepared using reverse transcriptase and the intra intron primer. Next the cDNA is then amplified using the PCR.

Figure 7A:
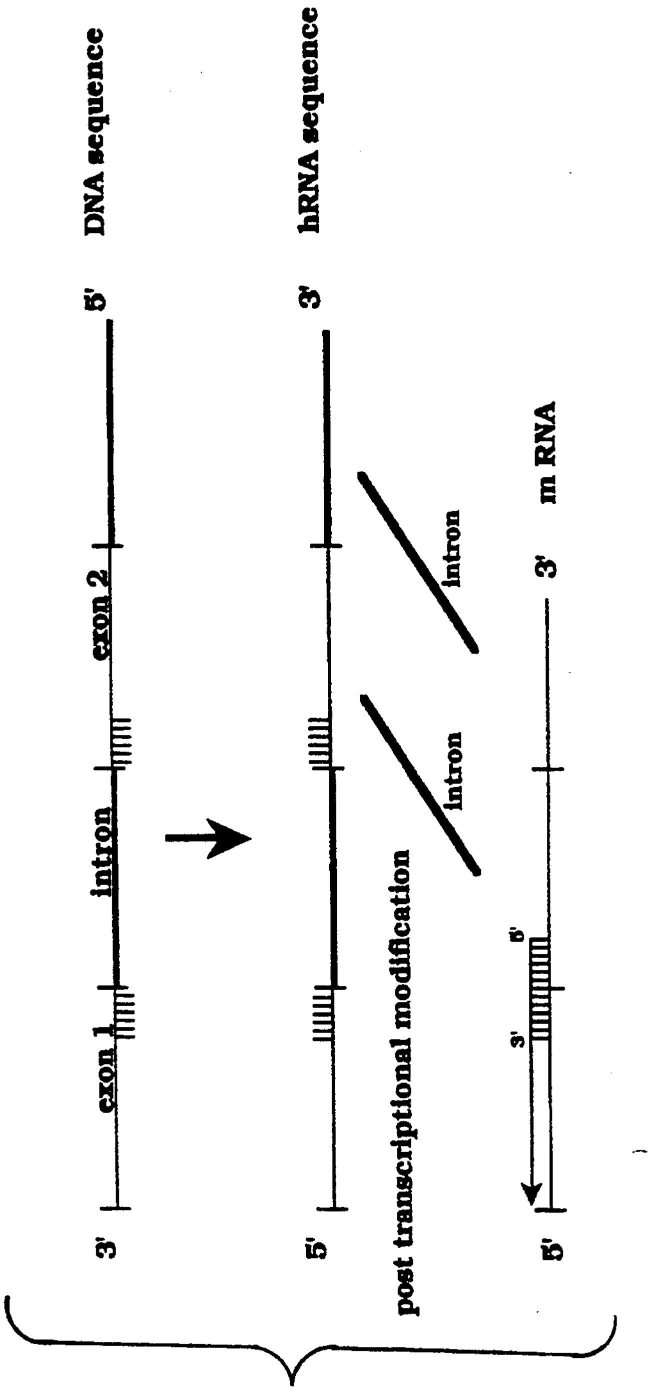
FIG. 7A shows splice point primers bridging intron sequences.
Figure 7B:
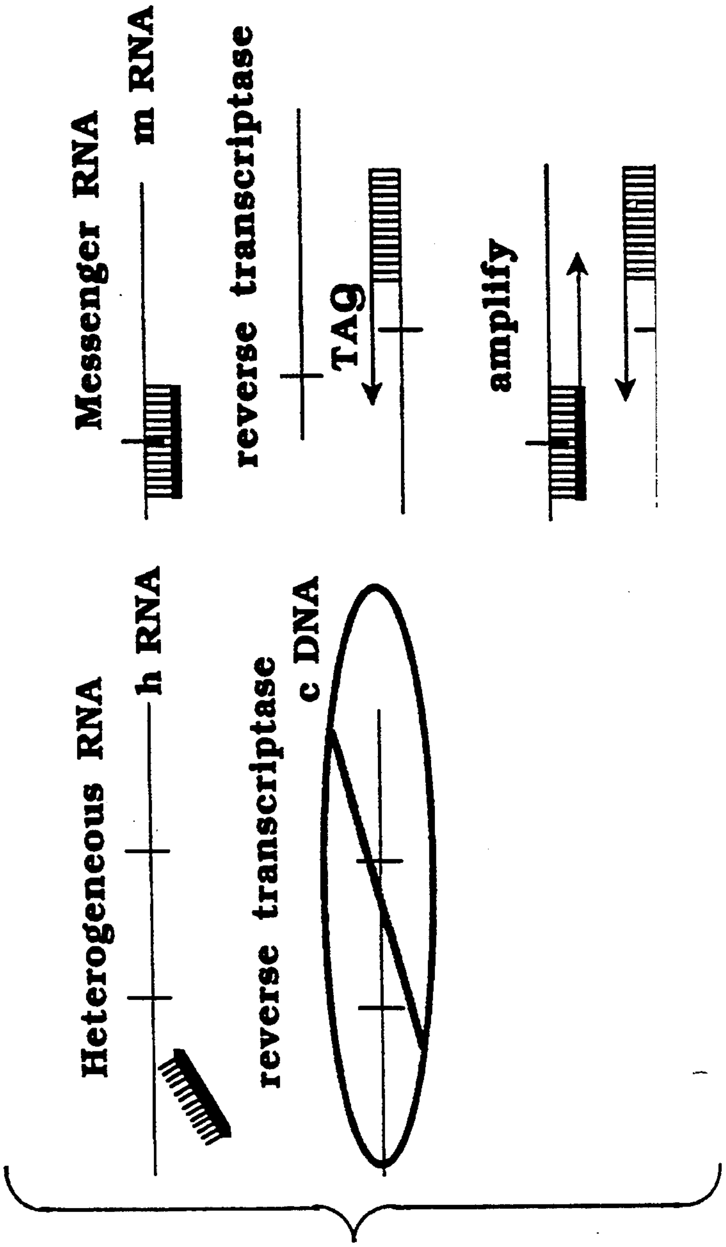
FIG. 7B depicts primers that bridge intron to specifically amplify messenger RNA (mRNA).

To specifically amplify mRNA, a cDNA is prepared using the splice point primers. As shown in FIG. 7A, both the gene and the hRNA are shown with coding sequences in exon 1 and exon 2 illustrated by the vertical lines separated by an intron. A primer of this sequence bridges across the intron so that when the intron is removed, it is homologous to the splice point sequence within the message. Such a strategy can also be employed to prepare primers to define gene rearrangements. As illustrated in FIG. 7B, in the presence of reverse transcriptase, the primer binds only to mRNA thereby producing a cDNA of messenger RNA that can be amplified by the PCR.

PCR Product Identification:

In order to demonstrate that the PCR can take place inside fixed cells, it was necessary to extract the product from the fixed cells and then visualize that product in some format. For the proof, a system was set up in which cytoskeletal actin mRNA transcripts in fixed L929 mouse fibroblast cells were transcribed into cDNAs using reverse transcription and then these cDNAs were amplified using the situ PCR. The cDNA was transcribed from the mRNA using the downstream primer ATG AGG TAG TCT GTC AGG TC SEQ ID NO:3 (A1#2) found at positions 551-569 (which corresponds to GenBank numbers 589-608) on γ-actin mRNA. For the PCR, the A1#2 primer and the upstream primer GCA TTG TCA CTA ACT GGG AC SEQ ID NO:4 (A0#1), found at positions 220-239 (which corresponds to GenBank numbers 260-279), were used to give a potential product of 345 base pairs (bp). $2.0\times10^6$ cells/sample were used for this experiment and they were cycled 35 times for the PCR.

After the in situ PCR, the cells were pelleted by centrifugation in a microcentrifuge. After removing the supernatant, the cells were then digested at 42° overnight in a lysis buffer (10 mM Tris-HCl, pH 8.0+10 mM EDTA (ethylenediaminetetraacetic acid)+50 mM NaCl+0.2% SDS (sodium dodecyl sulfate)) containing a protein diegesting enzyme, Proteinase k, at 200 ug/ml. The DNA was extracted from the digested matter using a standard phenol:chloroform: isoamylalochohol extraction as disclosed in Sambrook, J., Fritsch, E. F. and Mantiatis, T. *Molecular Cloning: A Laboratory Manual,* Second Edition. Cold Spring Harbor Laboratory Press, 1989. The amount of extracted DNA waas determined using the Dipstick kit from Invitrogen (Invitrogen San Diego, Calif. 92121).

Figure 8:
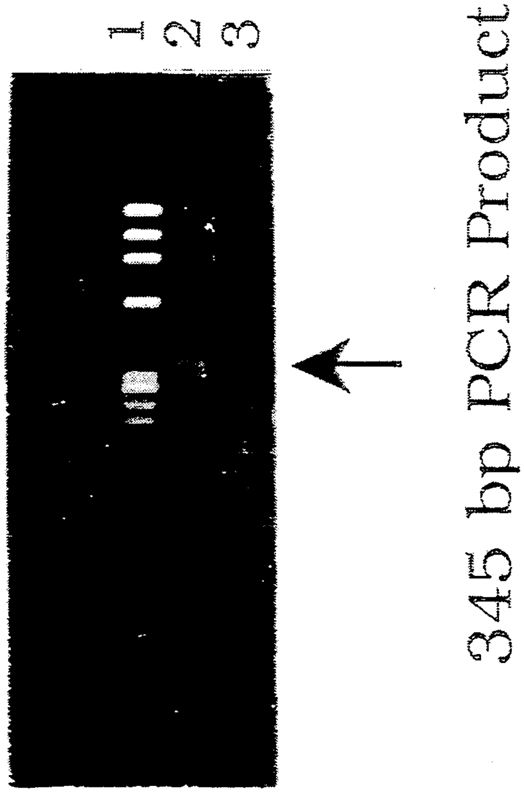
FIG. 8 shows DNA extracted from fixed cells after in situ PCR.

Samples of the extracted DNA were run on a 2.0% agarose gel containing 0.5 ug/ml ethidium bromide (a DNA stain). As seen in FIG. 8, an HAE III digest of phi-x174 DNA which is used as a size marker. From right to left, the highest band represented 1358 bp (base pairs) and the lowest band represents 72 bp. Lane two of the gel was DNA extracted from cells in which a complete in situ PCR was done and the band found midway down the gel, as compared to the markers, represented the 345 bp PCR product expected. In lane three of the gel, no reverse transcription step was done before the in situ PCR step during the procedure. A very faint band could be seen at the 345 bp level which may be due to amplification of genomic DNA. It is evident that the polymerase chain reaction did occur inside the fixed cells. There is also evidence, as found in many standard in vitro PCRs, of the production of nontarget products which will cause the smearing effect seen on the gel in lanes two and three.

While the invention has been described with respect to macrophages and fibroblast cells, the invention is useful with respect to many other cells such as disclosed in the Catalog of Cell Lines and Hybridomas from the American Type Culture Collection (ATCC Rockville Md. 20852-1776) the disclosure of which is incorporated herein by reference. A great potential of the process will be the rapid molecular phenotyping of cells by flow cytometry for detection of and management of human disease.

What is claimed is:

1. A process for measuring gene expression in intact mammalian cells which comprises performing a polymerase chain reaction in said cells wherein cell recovery is maximized by prevention of non-specific binding and amplified genetic material is caused to remain within the cells, comprising the steps of:

fixing the cells by suspension in a solution comprising ultrapure formaldehyde;

removing the cells from the solution comprising ultrapure formaldehyde;

adding a polymerase into the cells to amplify specific genetic material;

preventing loss of cells due to non-specific binding of cells to a reaction vessel;

and rapidly detecting the amplified genetic material in individual cells by flow cytometry.

2. The process of claim 1 wherein non-specific binding of cells to a reaction vessel is prevented by the addition of nuclease free bovine serum albumin.

* * * * *

SEQUENCE LISTING ( 1 ) GENERAL INFORMATION:

( i i i ) NUMBER OF SEQUENCES:4

( 2 ) INFORMATION FOR SEQ ID NO: 1:

( i ) SEQUENCE CHARACTERISTICS:
( A ) LENGTH: 32 bases
( B ) TYPE: nucleic acid
( C ) STRANDEDNESS: single
( D ) TOPOLOGY: linear ( i i ) MOLECULE TYPE: oligonucletide DNA ( i i i ) HYPOTHETICAL: no ( i v ) ANTI-SENSE: no ( v i ) ORIGINAL SOURCE:
( A ) ORGANISM: mus musculus ( i x ) FEATURE:
( A ) NAME/KEY: SEQ ID NO: 1: was taken from the Genbank listing for c-fos; file: musfos; and it is locat in the coding region of the c-fos gene. It is the complement of the listed sequence in the file.
( B ) LOCATION: bases 1389 - 1420

( x i ) SEQUENCE DESCRIPTION: SEQ ID NO: 1:

TTG CCC CTT CTG CCG ATG CTC TGC GCT CTG CC 32

( 2 ) INFORMATION FOR SEQ ID NO: 2:

( i ) SEQUENCE CHARACTERISTICS:
( A ) LENGTH: 31 bases
( B ) TYPE: nucleic acid
( C ) STRANDEDNESS: single
( D ) TOPOLOGY: linear ( i i ) MOLECULE TYPE: oligonucleotide DNA ( i i i ) HYPOTHETICAL: no ( i v ) ANTI-SENSE: no ( v i ) ORIGINAL SOURCE:
( A ) ORGANISM: mus musculus ( i x ) FEATURE:
( A ) NAME/KEY: SEQ ID NO: 2: was taken from the Genbank listing for c-fos; file: musfos; and it is -continued located in the coding region of the c-fos gene.
( B ) LOCATION: bases 1219 - 1249

( x i ) SEQUENCE DESCRIPTION: SEQ ID NO: 2:

TCC CCA CGG TGA CAG CCA TCT CCA CCA GCC C 31

( 2 ) INFORMATION FOR SEQ ID NO: 3:

( i ) SEQUENCE CHARACTERISTICS:
( A ) LENGTH: 20 bases
( B ) TYPE: nucleic acid
( C ) STRANDEDNESS: single
( D ) TOPOLOGY: linear ( i i ) MOLECULE TYPE: oligonucleotide DNA ( i i i ) HYPOTHETICAL: no ( i v ) ANTI-SENSE: no ( v i ) ORIGINAL SOURCE:
( A ) ORGANISM: mus musculus ( i x ) FEATURE:
( A ) NAME/KEY: SEQ ID NO: 3: was taken from the Genbank listing for g-actin; file: musactgcs; and it is located in the coding region of the g-actin sequence. It is the complement of the listed sequence in the file.
( B ) LOCATION: bases 589 - 608

( x i ) SEQUENCE DESCRIPTION: SEQ ID NO: 3:

ATG AGG TAG TCT GTC AGG TC 20

( 2 ) INFORMATION FOR SEQ ID NO: 4:

( i ) SEQUENCE CHARACTERISTICS:
( A ) LENGTH: 20 bases
( B ) TYPE: nucleic acid
( C ) STRANDEDNESS: single
( D ) TOPOLOGY: linear ( i i ) MOLECULE TYPE: oligonucleotide DNA ( i i i ) HYPOTHETICAL: no ( i v ) ANTI-SENSE: no ( v i ) ORIGINAL SOURCE:
( A ) ORGANISM: mus musculus ( i x ) FEATURE:
( A ) NAME/KEY: SEQ ID NO: 4: was taken from the Genbank listing for g-actin; file: musactgcs; and it is located in the coding region of the g-actin sequence.
( B ) LOCATION: bases 260- 279

( x i ) SEQUENCE DESCRIPTION: SEQ ID NO: 4:

GCA TTG TCA CTA ACT GGG AC 20